US009752102B2

(12) United States Patent
Mussmann et al.

(10) Patent No.: US 9,752,102 B2
(45) Date of Patent: Sep. 5, 2017

(54) LIQUID WASHING OR CLEANING AGENT CONTAINING PROTEASE AND AMYLASE

(71) Applicant: Henkel AG & Co. KGaA, Duesseldorf (DE)

(72) Inventors: Nina Mussmann, Willich (DE); Thomas Eiting, Duesseldorf (DE); Thorsten Bastigkeit, Wuppertal (DE); Konstantin Benda, Duesseldorf (DE); Hendrik Hellmuth, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 135 days.

(21) Appl. No.: 14/302,829

(22) Filed: Jun. 12, 2014

(65) Prior Publication Data

US 2014/0295522 A1 Oct. 2, 2014

Related U.S. Application Data

(63) Continuation-in-part of application No. PCT/EP2012/074883, filed on Dec. 10, 2012.

(30) Foreign Application Priority Data

Dec. 15, 2011 (DE) .................. 10 2011 088 751

(51) Int. Cl.
C11D 3/386 (2006.01)
C12N 9/54 (2006.01)

(52) U.S. Cl.
CPC ........... *C11D 3/38618* (2013.01); *C12N 9/54* (2013.01)

(58) Field of Classification Search
None
See application file for complete search history.

(56) References Cited

U.S. PATENT DOCUMENTS

| 7,300,782 | B2 | 11/2007 | Breves et al. |
| 2004/0259222 | A1 | 12/2004 | Breves et al. |
| 2012/0238005 | A1 | 9/2012 | Wieland et al. |

FOREIGN PATENT DOCUMENTS

| DE | 102009029513 | * | 3/2011 | ............ | C11D 3/386 |
| WO | 92/21760 | A1 | 12/1992 | | |
| WO | 95/23221 | A1 | 8/1995 | | |
| WO | 00/60060 | A2 | 10/2000 | | |
| WO | 2006/066596 | A2 | 6/2006 | | |
| WO | 2007/079938 | A2 | 7/2007 | | |

OTHER PUBLICATIONS

DE102009029513; Wieland et al, 2011, machine translation.*
Wieland et al, 2011, SEQ ID No. 1 from DE102009029513. Alignment with SEQ ID No. 1 herein w/ S3T, V4I, R99E, and V199I substitutions.*
Kottwitz et al, 2005. SEQ ID No. 2 from WO2005108537. Alignment withn SEQ ID No. 4 herein w/R118K D183deletion G184deletion N195F R320K R458/.*
Voigt et al, Rational evolutionary design: the theory of in vitro protein evolution. Adv Protein Chem. 2001;55:79-160.*
PCT International Search Report (PCT/EP2012/074883) dated May 13, 2013.
Sumner, "Dinitrosalicylic Acid: A Reagent for the Estimation of Sugar in Normal and Diabetic Urine", Journal of Biological Chemistry, vol. 47, pp. 5-9, 1921.
Sumner, "The Estimation of Sugar in Diabetic Urine, Using Dinitrosalicylic Acid", Journal of Biological Chemistry, vol. 62, pp. 287-290, 1924.
Gornall et al., "Determination of Serum Proteins by Means of the Biuret Reaction", Journal of Biological Chemistry, vol. 177, pp. 751-766, 1948.
Bender et al., "The Determination of the Concentration of Hydrolytic Enzyme Solutions: a-Chymotrypsin, Trypsin, Papain, Elastase, Subtilisin, and Acetylcholinesterase", Journal of the American Chemical Society, vol. 88:24, pp. 5890-5913, 1966.
Van Raay et al, "The Determination of Proteolytic Activity in Enzyme Concentrates and Enzyme Containing Detergents", Tenside Detergents, vol. 7, No. 3, pp. 125-132, 1970.
Delmar et al., "A Sensitive New Substrate for Chymotrypsin", Analytical Biochemistry, vol. 99, pp. 316-320, 1979.
Altschul et al., "Basic Local Alignment Search Tool", Journal of Molecular Biology, vol. 215, pp. 403-410, 1990.
Altschul et al., "Gapped BLAST and PSI-BLAST: A New Generation of Protein Database Search Programs", Nucleic Acids Research, vol. 25, No. 17, pp. 3389-3402, 1997.
Notredame et al., "T-Coffee: A Novel Method for Fast and Accurate Multiple Sequence Alignment", Journal of Molecular Biology, vol. 302, pp. 205-217, 2000.
Chenna et al., "Multiple Sequence Alignment with the Clustal Series of Programs", Nucleic Acids Research, vol. 31, No. 13, pp. 3497-3500, 2003.
Database Genbank [Online], May 12, 2011, XP002696855, Database accession No. AZG45768.
Database Genbank [Online], May 12, 2011, XP002696856, Database accession No. AZG45769.

* cited by examiner

*Primary Examiner* — Sheridan Swope
(74) *Attorney, Agent, or Firm* — Lorenz & Kopf, LLP

(57) ABSTRACT

The intention is to improve storage stability in a liquid washing or cleaning agent which contains a protease and amylase. This is achieved by using a protease which comprises an amino acid sequence which, over the entire length thereof, is at least 70% identical to the amino acid sequence stated in SEQ ID no. 1 and, in the numbering according to SEQ ID no. 1, has the amino acid substitution R99E or R99D in combination with at least two further amino acid substitutions which are selected from the group consisting of S3T, V4I and V199I.

9 Claims, No Drawings

LIQUID WASHING OR CLEANING AGENT CONTAINING PROTEASE AND AMYLASE

FIELD OF THE INVENTION

The present invention generally relates to liquid washing and cleaning agents, and more particularly relates to liquid enzyme-containing washing and cleaning agents which contain defined proteases in combination with an amylase, and furthermore proposes methods in which such agents are used. The invention furthermore relates to uses of defined proteases in liquid washing or cleaning agents which contain an amylase.

BACKGROUND OF THE INVENTION

The use of proteases of the subtilisin type is preferred for washing and cleaning agents. The proteases used in the washing or cleaning agents known from the prior art either originally originate from microorganisms, for instance of the genera *Bacillus, Streptomyces, Humicola*, or *Pseudomonas*, and/or are produced by suitable microorganisms using per se known biotechnological methods, for instance by transgenic expression hosts from the genera *Bacillus* or by filamentous fungi.

Further enzymes, in particular amylases, are increasingly present in particular in modern liquid washing agents. An amylase is an enzyme which catalyzes the hydrolysis of glycosidic bonds, in particular in polysaccharides such as starch. Among amylases, α-amylases, which hydrolyze the α(1-4)-glycosidic bonds in amylose are often used in washing and cleaning agents. Within the EC classification of enzymes, the numerical classification system for enzymes, α-amylases have the EC number ("Enzyme Commission number") 3.2.1.1 and consequently belong to the third of the six main classes of enzymes, the hydrolases (EC 3.-.-.-), then to the glycosylases (EC 3.2.-.-) and in turn to the glycosidases (EC 3.2.1.-), i.e. enzymes which hydrolyze O- and/or S-glycosyl compounds. Starch breakdown by α-amylases gives rise to dextrins and, from the latter, maltose, glucose and branched oligosaccharides. Amylases consequently in particular act against starch-containing residues on laundry and catalyze the hydrolysis thereof.

International patent applications WO95/23221 and WO92/21760 disclose variants of the alkaline protease from *Bacillus lentus* DSM 5483 which are suitable for use in washing or cleaning agents, as well as washing and cleaning agents containing such proteases. International patent application WO2011/032988 furthermore discloses washing and cleaning agents which likewise contain variants of the alkaline protease from *Bacillus lentus* DSM 5483. The protease variants disclosed in said documents may be modified, in addition to further positions, in positions 3, 4, 99 and 199 in the numbering system for the alkaline protease from *Bacillus lentus* DSM 5483 and for example have amino acids 3T, 4I, 99D, 99E or 199I in the stated positions. It is furthermore disclosed that the washing agents may contain further enzymes, also including an amylase. The washing agents may be solid or liquid. Said document does not, however, directly and unambiguously disclose a liquid washing agent which contains an amylase in combination with a protease which has combinations of these modifications as are described hereinafter.

A disadvantage of prior art protease- and amylase-containing liquid washing and cleaning agents is that they have inadequate storage stability and they accordingly lose a considerable degree of enzymatic, in particular amylolytic and/or proteolytic, activity after only a short time. The presence of protease frequently leads to the loss of amylolytic activity, since the protease inactivates the amylase. The washing or cleaning agent then no longer exhibits optimum cleaning performance.

It is an object of the present invention to overcome the stated disadvantage and to provide protease- and amylase-containing liquid washing or cleaning agents which have adequate or improved storage stability, in particular with regard to their enzymatic and preferably their amylolytic and/or proteolytic activity.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A liquid washing or cleaning agent comprising a protease which comprises an amino acid sequence which, over the entire length thereof, is at least 70% identical to the amino acid sequence stated in SEQ ID no. 1 and, in the numbering according to SEQ ID no. 1, has the amino acid substitution R99E or R99D in combination with at least two further amino acid substitutions which are selected from the group consisting of S3T, V4I and V199I; and an amylase.

Use of a protease which comprises an amino acid sequence which, over the entire length thereof, is at least 70% identical to the amino acid sequence stated in SEQ no. 1 and, in the numbering according to SEQ ID no. 1, has the amino acid substitution R99E or R99D in combination with at least two further amino acid substitutions which are selected from the group consisting of S3 T, V4I and V199I, in order to provide a proteolytic activity in a liquid washing or cleaning agent which comprises an amylase.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention accordingly provides a liquid washing or cleaning agent comprising (a) a protease which comprises an amino acid sequence which, over the entire length thereof, is at least 70% identical to the amino acid sequence stated in SEQ ID no. 1 and, in the numbering according to SEQ ID no. 1, has the amino acid substitution R99E or R99D in combination with at least two further amino acid substitutions which are selected from the group consisting of S3T, V4I and V199I, and (b) an amylase.

It has surprisingly been found that a liquid washing or cleaning agent which contains the combination of such a protease with an amylase is advantageously stable in storage. In particular, it exhibits improved cleaning performance, in particular improved amylolytic and/or proteolytic cleaning performance, after storage in comparison with a washing or cleaning agent which differs from an agent according to the invention merely by the protease present in the respective agent, wherein at the start of storage the protease is present in the agents to be compared in an identical concentration relative to active enzyme. A protease provided for the purposes of the present invention therefore leads to reduced inactivation of the amylase and itself also exhibits reduced loss of performance. The reduced inactivation of amylase and/or protease by the protease provided for the purposes of the present invention is, however, not due to inadequate protease performance and/or activity.

An agent according to the invention preferably exhibits in this respect cleaning performance on protease-sensitive soiling which remains good, in particular advantageous. Such an agent therefore enables satisfactory or improved removal of at least one, preferably of a plurality of protease-sensitive types of soiling on textiles and/or hard surfaces, for example dishes. In selected developments of the invention, such cleaning performance with regard to at least one protease-sensitive type of soiling in particular also occurs at low temperatures, for example between 10° C. and 50° C., between 10° C. and 40° C. or between 20° C. and 40° C.

With regard to the international patent applications WO95/23221, WO92/21760 and WO2011/032988 mentioned in the introduction, the present invention is thus a particularly advantageous selection which results in a liquid washing agent being obtained which has good performance and is stable in storage, in particular with regard to the proteolytic and/or amylolytic cleaning performance of the agent after storage and/or with regard to the proteolytic and/or amylolytic activity of the agent after storage.

For the purposes of the invention, cleaning performance is taken to mean the ability of the washing or cleaning agent partially or completely to remove soiling which is present on application of the agent. In the case of laundry soiling, this is preferably lightening performance with regard to one or more types of soiling on textiles. Examples of laundry soiling are blood-milk/ink on cotton, whole egg/pigment on cotton, chocolate-milk/ink on cotton, peanut oil-pigment/ink on polyester/cotton, grass on cotton or cocoa on cotton. In the case of dishwashing agents, cleaning performance describes the ability of the dishwashing agent to remove soiling which is present from the hard surfaces of the dishes. Examples of crockery soiling are milk, minced meat, egg yolk, porridge oats and starch. For the purposes of the invention, both the washing or cleaning agent comprising the protease and the amylase or the washing liquor formed by this agent, and the protease or amylase themselves exhibit a respective cleaning performance. The cleaning performance of the enzymes thus contributes to the cleaning performance of the agent or of the washing liquor formed by the agent. Amylolytic cleaning performance refers to cleaning performance on amylase-sensitive soiling. Proteolytic cleaning performance refers to cleaning performance on protease-sensitive soiling. Cleaning performance is determined in conventional manner, preferably as stated further below.

The washing liquor is understood to be the working solution containing the washing or cleaning agent, which solution acts on textiles or fabric or hard surfaces and thus comes into contact with the soiling present on textiles or fabrics or hard surfaces. The washing liquor conventionally arises when the washing or cleaning process begins and the washing or cleaning agent is diluted with water for example in a dishwashing machine, a washing machine or in another suitable container.

Storage stability for the purposes of the invention is in particular obtained when a washing or cleaning agent according to the invention exhibits greater cleaning performance after storage in comparison with a control composition which differs from the washing or cleaning agent according to the invention solely by the protease present in the control composition. At the beginning of storage, the two agents to be compared therefore have the same quantity or concentration of amylase and/or initial amylolytic activity. Furthermore, at the beginning of storage, the protease is present in both agents in an identical concentration, relative to active enzyme, and the two agents are treated in identical manner, in particular with regard to storage conditions and determination of enzyme activity. Storage lasts increasingly preferably for at least 24 hours, 48 hours, 72 hours, 5 days, 1 week, 2 weeks, 3 weeks or 4 weeks. Storage furthermore preferably proceeds at a temperature of 20° C., 30° C. or 40° C., more preferably at 40° C.

Enzyme activity may be determined in this respect, depending on the particular enzyme type, in conventional manner. Methods for determining activity are familiar to a person skilled in the art in the field of enzyme technology and are routinely used by such persons. Methods for determining protease activity are for example disclosed in Tenside [Surfactants], volume 7 (1970), pages 125-132. Proteolytic activity may furthermore be determined on the basis of the liberation of the chromophore para-nitroaniline (pNA) from the substrate suc-L-Ala-L-Ala-L-Pro-L-Phe-p-nitroanilide (suc-AAPF-pNA) The protease cleaves the substrate and liberates pNA. Liberation of the pNA brings about an increase in absorbance at 410 nm, the time profile of which is a measure of enzymatic activity (cf. Del Mar et al., 1979). The measurement is carried out at a temperature of 25° C., at pH 8.6 and a wavelength of 410 nm. The measurement time amounts 5 min with a measurement interval of 20 s to 60 s. Protease activity is preferably stated in PU (protease units).

Amylase activity is determined in conventional manner. Amylase activity is preferably determined as stated below. Amylases convert starch into glucose. Under defined reaction conditions (tris-maleate buffer pH 6.5, 50° C., 15 min), the samples to be investigated are incubated with 0.67% starch (soluble, pretreated using the Zulkowsky method (treated with glycerol at 190° C.)). By addition of dinitrosalicylic acid and heating to 100° C., said acid is reduced by glucose and other reducing sugars under alkaline conditions to form an orange-red dye which is determined photometrically at 540 nm after completion of the reaction. The quantity of liberated sugar corresponding to the color is here a measure of enzyme activity (cf. Sumner et al., J. Biol. Chem., 1921, 47 & 1924, 62).

The presence of enzyme stabilization for the purposes of the present invention is more preferably determined as stated above using a protease- and amylase-containing liquid washing or cleaning agent which is stored for four weeks at a temperature of 40° C., wherein proteolytic activity is determined via the liberation of the chromophore para-nitroaniline (pNA) from the substrate suc-AAPF-pNA, and amylolytic activity is determined as stated above.

The protease present in a washing or cleaning agent according to the invention comprises an amino acid sequence which, over the entire length thereof, is at least 70% identical to the amino acid sequence stated in SEQ ID no. 1 and, in the numbering according to SEQ ID no. 1, has the amino acid substitution R99E or R99D in combination with at least two further amino acid substitutions which are selected from the group consisting of S3T, V4I and V199I.

In a further embodiment of the invention, the protease comprises an amino acid sequence which, over the entire length thereof, is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence stated in SEQ ID no. 1 and, in the numbering according to SEQ ID no. 1, has the amino acid substitution R99E in combination with at least two further amino acid substitutions selected from the group consisting of S3T, V4I and V199I.

In a further embodiment of the invention, the protease comprises an amino acid sequence which, over the entire length thereof, is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence stated in SEQ ID no. 1 and, in the numbering according to SEQ ID no. 1, has the amino acid substitution R99D in combination with at least two further amino acid substitutions selected from the group consisting of S3T, V4I and V199I.

SEQ ID no. 1 is the sequence of the mature alkaline protease from *Bacillus* lentos DSM 5483, which is disclosed in international patent application WO92/21760, and to the disclosure of which reference is expressly made.

Proteases which are more preferred according to the invention are: a protease comprising an amino acid sequence which, over the entire length thereof, is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence stated in SEQ ID no. 1 and, in the numbering according to SEQ ID no. 1, has the amino acid substitution R99E in combination with the amino acid substitutions S3T and V4I, in particular a protease according to SEQ ID no. 1 with the amino acid substitutions S3T, V4I and R99E;

a protease comprising an amino acid sequence which, over the entire length thereof, is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence stated in SEQ ID no. 1 and, in the numbering according to SEQ ID no. 1, has the amino acid substitution R99E in combination with the amino acid substitutions S3T and V199I, in particular a protease according to SEQ ID no. 1 with the amino acid substitutions S3T, R99E and V199I;

a protease comprising an amino acid sequence which, over the entire length thereof, is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence stated in SEQ ID no. 1 and, in the numbering according to SEQ ID no. 1, has the amino acid substitution R99E in combination with the amino acid substitutions V4I and V199I, in particular a protease according to SEQ ID no. 1 with the amino acid substitutions V4I, R99E and V199I;

a protease comprising an amino acid sequence which, over the entire length thereof, is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence stated in SEQ ID no. 1 and, in the numbering according to SEQ ID no. 1, has the amino acid substitution R99D in combination with the amino acid substitutions S3T and V4I, in particular a protease according to SEQ ID no. 1 with the amino acid substitutions S3T, V4I and R99D;

a protease comprising an amino acid sequence which, over the entire length thereof, is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence stated in SEQ ID no. 1 and, in the numbering according to SEQ ID no. 1, has the amino acid substitution R99D in combination with the amino acid substitutions S3T and V199I, in particular a protease according to SEQ ID no. 1 with the amino acid substitutions S3T, R99D and V199I;

a protease comprising an amino acid sequence which, over the entire length thereof, is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence stated in SEQ ID no. 1 and, in the numbering according to SEQ ID no. 1, has the amino acid substitution R99D in combination with the amino acid substitutions V4I and V199I, in particular a protease according to SEQ ID no. 1 with the amino acid substitutions V4I, R99D and V199I.

Further more preferred embodiments of proteases according to the invention are distinguished in that they have the amino acid substitution R99E or R99D in combination with the three further amino acid substitutions S3T, V4I and V199I. The following proteases are particularly preferred in this respect:

a protease comprising an amino acid sequence which, over the entire length thereof, is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98% and 98.5% identical to the amino acid sequence stated in SEQ ID no. 1 and, in the numbering according to SEQ ID no. 1, has the amino acid substitution R99E in combination with the amino acid substitutions S3T, V4I and V199I, in particular a protease according to SEQ ID no. 1 with the amino acid substitutions S3T, V4I, R99E and V199I. Such a protease is stated in SEQ ID no. 2;

a protease comprising an amino acid sequence which, over the entire length thereof, is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98% and 98.5% identical to the amino acid sequence stated in SEQ ID no. 1 and, in the numbering according to SEQ ID no. 1, has the amino acid substitution R99D in combination with the amino acid substitutions S3T, V4I and V199I, in particular a protease according to SEQ ID no. 1 with the amino acid substitutions S3T, V4I, R99D and V199I. Such a protease is stated in SEQ ID no. 3.

Further more preferred proteases are proteases as described above which furthermore have the amino acid leucine (L) at position 211 in the numbering according to SEQ ID no. 1.

The amino acid positions are defined for the purposes of the present invention by an alignment of the amino acid sequence of the protease to be used with the amino acid sequence of the protease from *Bacillus lentus*, as stated in SEQ ID no. 1. Since the protease from *Bacillus lentus* in the prior art constitutes an important reference molecule for describing proteases and amino acid changes, it is advantageous to refer to the numbering of the protease from *Bacillus lentus* (SEQ ID no. 1) in amino acid position assignment. The numbering is furthermore based on the mature protein. This assignment should in particular also be used if the amino acid sequence of the protease to be used comprises a larger number of amino acid residues than the protease from *Bacillus lentus* according to SEQ ID no. 1. On the basis of the stated positions in the amino acid sequence of the protease from *Bacillus lentus*, the amino acid positions in a protease to be used according to the invention are those which are assigned to precisely these positions in an alignment.

In addition to position 99, particularly advantageous positions should accordingly be assigned to positions 3, 4, 199 and 211, in an alignment with SEQ ID no. 1 and thus in the numbering according to SEQ ID no. 1. The stated positions are occupied by the following amino acid residues in the wild-type molecule of the protease from *Bacillus lentus*: S3, V4, V199, and L211. Depending on the number of sequence deviations from SEQ ID no. 1 which are present, different maximum identity values therefore arise which a protease to be used according to the invention in SEQ ID no. 1 may exhibit, even should it match SEQ ID no. 1 with regard to all other amino acids. This factor should be taken into account for every possible combination of the proposed sequence modifications in each individual case and is furthermore also dependent on the length of the amino acid sequence of the protease. For example, with one, two, three, four, five, six, seven, eight or nine sequence modifications, maximum identity amounts to 98.88%, 98.51%, 98.14%, 97.77%, 97.40%, 97.03% or 96.65% respectively for an amino acid sequence 269 amino acids in length, or to 98.91%, 98.55%, 98.18%, 97.82%, 97.45%, 97.09% or 96.73% respectively for an amino acid sequence 275 amino acids in length.

According to the invention it has been found that through the addition of such a protease to a liquid washing or cleaning agent containing an amylase, a particularly storage-stable liquid washing agent is obtained, in particular with regard to its residual cleaning performance after storage, in particular after a storage period of increasingly preferably 24 hours, 48 hours, 72 hours, 5 days, 1 week, 2 weeks, 3 weeks or 4 weeks.

A protease contained in a washing or cleaning agent according to the invention exhibits proteolytic activity, i.e. it is capable of hydrolyzing peptide bonds of a polypeptide or protein. It is therefore an enzyme which catalyzes the hydrolysis of peptide bonds and is thus capable of cleaving peptides or proteins. It is in particular a subtilase and more preferably a subtilisin.

An amylase is an enzyme as described in the introduction. Amylases may be designated by synonyms, for example 1,4-alpha-D-glucan glucanohydrolase or glycogenase. Amylases which can be formulated according to the invention are preferably α-amylases. Whether an enzyme is an α-amylase for the purposes of the invention is decided by its ability to hydrolyze α(1-4)-glycosidic bonds in the amylose of starch.

Examples of amylases formulatable according to the invention are the α-amylases from *Bacillus licheniformis*, from *Bacillus amyloliquefaciens* or from *Bacillus stearothermophilus* and in particular the further developments thereof enhanced for use in washing or cleaning agents. The enzyme from *Bacillus licheniformis* is obtainable from Novozymes under the name Termamyl® and from Danisco/Genencor under the name Purastar®ST. Further developed products of this α-amylase are obtainable from Novozymes under the trade name Duramyl® and Termamyl®ultra, from Danisco/Genencor under the name Purastar®OxAm and from Daiwa Seiko Inc., Tokyo, Japan, as Keistase®. The α-amylase from *Bacillus amyloliquefaciens* is distributed by Novozymes under the name BAN®, and variants derived from the α-amylase from *Bacillus stearothermophilus* are distributed under names BSG® and Novamyl®, likewise by Novozymes. Particular note should furthermore be taken for this purpose of the α-amylase from *Bacillus* sp. A 7-7 (DSM 12368) and the cyclodextrin glucanotransferase (CGTase) from *Bacillus agaradherens* (DSM 9948). Fusion products of all the stated molecules may likewise be used. Furthermore, the further developments of α-amylase from *Aspergillus niger* and *A. oryzae* obtainable under the trade name Fungamyl® from Novozymes are also suitable. Further commercial products which may advantageously be used are for example Amylase-LT® and Stainzyme® or Stainzyme Ultra® or Stainzyme Plus®, the latter likewise from Novozymes. Variants of these enzymes obtainable by point mutations may also be used according to the invention. More preferred amylases are disclosed in international published patent applications WO00/60060, WO03/002711, WO03/054177 and WO07/079,938, to the disclosure of which reference is therefore explicitly made or the disclosure content of which is therefore explicitly included in the present patent application.

More preferred amylases, having at least about 96%, preferably at least about 97%, more preferably at least about 98%, even more preferably at least about 99%, identity to SEQ ID NO: 4 herein are disclosed in international published patent application WO00/60060, said preferred amylases are incorporated by reference herein.

α-Amylase variants of α-amylase AA560 according to SEQ ID no. 4 are particularly suitable for use in agents according to the invention. The following variants are particularly advantageous:

(a) α-amylase variant which, relative to the α-amylase AA560 according to SEQ ID no. 4, has one, two, three, four, five or six of the following sequence modifications in the numbering of α-amylase AA560: R118K, D183* (deletion), G184* (deletion), N195F, R320K, R458K. The α-amylase variant more preferably has all six of the stated sequence modifications;

(b) α-amylase variant which, relative to the α-amylase AA560 according to SEQ ID no. 4, has the following sequence modifications (in the numbering of α-amylase AA560):
   (1) M9L/M202I,
   (2) M9L/M202I/M323T,
   (3) M9L/M202I/M323T/M382Y,
   (4) M9L/M202I/Y295F/A339S,
   (5) M9L/M202I/Y295F,
   (6) M9L/M202I/A339S,
   (7) M9L/M202I/Y295F/A339S,
   (8) M9L/M202I/Y295F/A339S/E345R,
   (9) M9L/G149A/M202I/Y295F/A339S/E345R,
   (10) M9L/M202L,
   (11) M9L/M202L/M323T,
   (12) M9L/M202L/M323T/M382Y,
   (13) M9L/M202L/Y295F/A339S,
   (14) M9L/M202L/Y295F,
   (15) M9L/M202L/A339S,
   (16) M9L/M202L/Y295F/A339S,
   (17) M9L/M202L/Y295F/A339S, E345R,
   (18) M9L/G149A/M202L/Y295F/A339S/E345R,
   (19) M9L/M202T,

(20) M9L/M202T/M323T,
(21) M9L/M202T/M323T/M382Y,
(22) M9L/M202T/Y295F/A339S,
(23) M9L/M202T/Y295F,
(24) M9L/M202T/A339S,
(25) M9L/M202T/Y295F/A339S,
(26) M9L/M202T/Y295F/A339S/E345R,
(27) M9L/G149A/M202T/Y295F/A339S/E345R,
(28) M9L/G149A/M202I/V214T/Y295F/N299Y/M323T/A339S/E345R,
(29) M9L/G149A/M202L/V214I/Y295F/M323T/A339S/E345R/M382Y,
(30) M9L/G149A/G182T/0186A/M202I/V214I/Y295F/N299Y/M323T/A339S,
(31) M9L/G149A/G182T/G186A/M202L/T257I/Y295F/N299Y/M323T/A339S/E345R,
(32) M9L/G149A/M202L/V214T/Y295F/N299Y/M323T/A339S/E345R,
(33) M9L/G149A/M202I/V214I/Y295F/M323T/A339S/E345R/M382Y,
(34) M9L/G149A/G182T/G186A/M202L/V214I/Y295F/N299Y/M323T/A339S,
(35) M9L/0149A/G182T/G186A/M202I/T257I/Y295F/N299Y/M323T/A339S/E345R,
(36) M9L/G149A/M202I/V214T/Y295F/N299Y/M323T/A339S/E345R/N471E,
(37) M9L/G149A/M202L/V214I/Y295F/M323T/A339S/E345R/M382Y/N471E,
(38) M9L/G149A/G182T/G186A/M202I/V214I/Y295F/N299Y/M323T/A339S/N471E,
(39) M9L/G149A/G182T/G186A/M202L/T257I/Y295F/N299Y/M323T/A339S/E345R/N471E,
(40) M202L/M105F/M208F,
(41) G133E/M202L/Q361E,
(42) G133E/M202L/R444E,
(43) M202L/Y295F,
(44) M202L/A339S,
(45) M202L/M323T,
(46) M202L/M323T/M309L,
(47) M202L/M323T/M430I,
(48) M202L/V214T/R444Y,
(49) M202L/N283D/Q361E,
(50) M202L/M382Y/K383R,
(51) M202L/K446R/N484Q,
(52) M202I/Y295F,
(53) M202I/A339S,
(54) M202I/M105F/M208F,
(55) G133E/M202I/Q361E,
(56) G133E/M202I/R444E,
(57) M202I/M323T,
(58) M202I/M323T/M309L,
(59) M202I/M323T/M430I,
(60) M202I/V214T/R444Y,
(61) M202I/N283D/Q361E,
(62) M202I/M382Y/K383R,
(63) M202I/K446R/N484Q,
(64) M202V/M105F/M208F,
(65) G133E/M202V/Q361E,
(66) G133E/M202V/R444E,
(67) M202V/M323T,
(68) M202V/M323T/M309L,
(69) M202V/M323T/M430I,
(70) M202V/M323T/M9L,
(71) M202V/V214T/R444Y,
(72) M202V/N283D/Q361E,
(73) M202V/M382Y/K383R,
(74) M202V/K446R/N484Q,
(75) M202T/M105F/M208F,
(76) G133E/M202T/Q361E,
(77) G133E/M202T/R444E,
(78) M202T/Y295F,
(79) M202T/A339S,
(80) M202T/M323T,
(81) M202T/M323T/M309L,
(82) M202T/M323T/M430I,
(83) M202T/M323T/M9L,
(84) M202T/V214T/R444Y,
(85) M202T/N283D/Q361E,
(86) M202T/A339S,
(87) M202T/Y295F
(88) M202T/N299F,Y,
(89) M202T/M382Y/K383R or
(90) M202T/K446R/N484Q.

Among these, the following α-amylase variants are particularly preferred:
(10) M9L/M202L,
(28) M9L/G149A/M202I/V214T/Y295F/N299Y/M323T/A339S/E345R,
(31) M9L/G149A/G182T/G186A/M202L/T257I/Y295F/N299Y/M323T/A339S/E345R,
(35) M9L/G149A/0182T/0186A/M202I/T257I/Y295F/N299Y/M323T/
(38) M9L/G149A/G182T/G186A/M202I/V214I/Y295F/N299Y/M323T/
(39) M9L/G149A/G182T/G186A/M202L/T257I/Y295F/N299Y/M323T/A339S/E345R/N471E,
(45) M202L/M323T,
(46) M202L/M323T/M309L,
(62) M202I/M382Y/K383R,
(68) M202V/M323T/M309L,
(73) M202V/M382Y/K383R
(82) M202T/M323T/M430I or
(84) M202T/V214T/R444Y.

(c) α-amylase variant according to (b) which additionally has all six of the sequence modifications stated in (a), particularly preferably variant 31 with the six sequence modifications stated in (a).

The α-amylase variant stated in (a) and the α-amylase variant 31 stated in (c) with the six sequence modifications stated in (a) are particularly preferred according to the invention.

The identity of nucleic acid or amino acid sequences is determined by a sequence comparison. Such a comparison proceeds by assigning similar sequences to one another in the nucleotide sequences or amino acid sequences. This sequence comparison is preferably performed on the basis of the conventionally used BLAST algorithm established in the prior art Altschul, S. F., Gish, W., Miller, W., Myers, E. W. & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pp. 3389-3402) and in principle proceeds by assigning similar sequences of nucleotides or amino acids in the nucleic acid or amino acid sequences to one another. A tabular assignment of the positions in question is known as an alignment. A further algorithm available in the prior art is the FASTA algorithm. Sequence comparisons (alignments), in particular multiple sequence comparisons, are conventionally created using computer software. Use is often made for example of the Clustal series (cf. for example Chema et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-217) or programs which are based on these programs or algorithms. For the purposes of the present invention sequence comparisons and alignments are preferably performed with the computer program Vector NTI® Suite 10.3 (Invitrogen Corporation, 1600 Faraday Avenue, Carlsbad, Calif., USA) using the preset default parameters.

Such a comparison allows a statement to be made about the similarity of the compared sequences. It is conventionally stated in percent identity, i.e. the proportion of identical nucleotides or amino acid residues therein or in an alignment of mutually corresponding positions. The broader term "homology" also includes consideration of amino acid substitutions conserved in amino acid sequences, thus amino acids with similar characteristics, since they generally have similar activities or functions within the protein. The similarity of the compared sequences may therefore also be stated in percent homology or percent similarity. Statements regarding identity and/or homology may be made over entire polypeptides or genes or only over individual domains. Homologous or identical domains of various nucleic acid or amino acid sequences are therefore defined by matches in the sequences. They often have identical or similar functions. They may be small and comprise only a few nucleotides or amino acids. Often such small domains exercise functions which are essential for the overall activity of the protein. It may therefore be meaningful to relate sequence matches only to individual, optionally small domains. If not stated otherwise, however, statements regarding identity or homology in the present application relate to the entire length of the nucleic acid or amino acid sequence indicated in each case.

In a further embodiment of the invention, a washing or cleaning agent according to the invention is furthermore characterized in that its cleaning performance at least corresponds to that of a washing or cleaning agent which contains a protease which comprises an amino acid sequence which corresponds to the amino acid sequence stated in SEQ ID no. 2 or SEQ ID no. 3, more preferably to that stated in SEQ ID no. 2. Cleaning performance is determined in a washing system which contains an amylase-containing washing agent at a rate of addition of between 4.0 and 11.0 grams per liter of washing liquor and which contains the protease, wherein the proteases to be compared are used at identical concentration (relative to active protein) and the cleaning performance is determined relative to minced meat and/or egg yolk soiling on dishes by determining the remaining residues of the respective soiling after the washing process, the washing process proceeds for at least 30 minutes, preferably 60 minutes, at a temperature of 50° C. and the water has a water hardness of between 15.5 and 16.5° dH (German hardness degrees).

The washing agent for the washing system is preferably a biphasic liquid automatic dishwashing agent which is of the following composition (all values stated in weight percent):
(a) Enzyme Phase:

| Builder | 15.0-20.0 |
| Sugar alcohol | 8.0-12.0 |
| Nonionic surfactant ($C_8$-$C_{10}$ fatty alcohol ethoxylate with 22 EO) | 3.0-5.0 |
| Alkali compound (base) | 3.0-4.0 |
| Boric acid | 2.5-3.5 |
| Phosphonate (HEDP) | 1.5-2.5 |

-continued

| Amylase | 1.0-2.0 |
| Protease | see text |
| Ca salt | 0.8-1.2 |
| Zn salt | 0.15-0.25 |
| Thickener | 0.8-1.2 |
| Dye, perfume, preservative | 0.25-0.5 |
| Water | ad 100 |

The amylase is preferably the preparation of an α-amylase variant which, relative to the α-amylase AA560 according to SEQ ID no. 4, has the following sequence modifications in the numbering of α-amylase AA560: R118K, D183* (deletion), G184* (deletion), N195F, R320K, R458K (Novozymes).
(b) Alkaline Phase:

| Builder | 7.5-12.5 |
| Sodium carbonate | 7.5-12.5 |
| Sulfopolymer | 5.0-8.0 |
| Alkali compound (base) | 3.0-5.0 |
| Monoethanolamine | 2.0-4.0 |
| Phosphonate (HEDP) | 2.0-5.0 |
| Thickener | 0.8-1.2 |
| Dye, perfume, preservative | 0.25-0.5 |
| Water | ad 100 |

The protease is present in the agent in a concentration of 0.01-1 wt. %, preferably of 0.1 to 0.5 wt. %, relative to active protein. The two phases are apportioned in identical proportions (in each case 20 g per phase) for a washing cycle in a dishwashing machine. Washed is performed in a pH value range between pH 9 and pH 10 in a conventional dishwashing machine, for example a G698SC dishwashing machine from Miele. Neither protease nor amylase activity in the washing liquor are equal to zero at the beginning of washing.

Cleaning performance is evaluated visually using the standard IKW method on a scale from 1 to 10, wherein a value of 10 is the best rating (no discernible residue).

Cleaning performance is more preferably determined in a dishwashing machine relative to minced meat and egg yolk soiling on dishes using a biphasic liquid automatic dishwashing agent as described above.

In a further embodiment of the invention, a washing or cleaning agent according to the invention is furthermore characterized in that its storage stability at least corresponds to that of a washing or cleaning agent which contains a protease which comprises an amino acid sequence which corresponds to the amino acid sequence stated in SEQ ID no. 2 or SEQ ID no. 3, more preferably to that stated in SEQ ID no. 2. Such storage stability is present if, after storage for four weeks at 50° C., the washing or cleaning agent according to the invention has an identical or greater cleaning performance than the washing or cleaning agent to be used by way of comparison, wherein the agent according to the invention differs from the washing or cleaning agent to be used by way of comparison only by the protease contained therein.

The agent to be used by way of comparison more preferably comprises a biphasic liquid automatic dishwashing agent as stated above, wherein the cleaning performance is determined as stated above.

At the beginning of storage, both agents to be compared have the identical initial amylolytic activity, contain the protease in an identical concentration relative to active enzyme, and both agents are treated in the same manner.

Proteolytic activity in the agents is in each case determined via the liberation of the chromophore para-nitroaniline (pNA) from the substrate suc-AAPF-pNA, and the amylolytic activity thereof is in each case determined as stated above. The initial activities for the protease and the amylase in the respective agent are not equal to zero.

Using the amylase at identical activity and the proteases at identical concentration, relative to active protein, ensures that, even in the event of any divergence in the ratio of active substance to total protein (specific activity values), it is the enzymatic properties actually present which are compared.

Unless otherwise stated, for the purposes of the present invention, reference is in each case made to the weight of the liquid washing agent, i.e. the values are stated relative to the weight thereof.

Numerous proteases and in particular subtilisins are formed as "preproteins", i.e. accompanied by a propeptide and a signal peptide, wherein the function of the signal peptide conventionally consists in ensuring export of the protease from the cell producing it into the periplasm or the medium surrounding the cell, and the propeptide is conventionally necessary for correct folding of the protease. The signal peptide and the propeptide are as a rule the N-terminal part of the preprotein. The signal peptide is cleaved under natural conditions from the rest of the protease by a signal peptidase. Correct, final, propeptide-assisted folding of the protease then takes place. The protease is then in its active form and itself cleaves off the propeptide. Once the propeptide has been cleaved off, the then mature protease, in particular subtilisin, exercises its catalytic activity without the originally present N-terminal amino acids. For industrial applications in general and in particular for the purposes of the invention, the mature proteases, i.e. the enzymes processed after production thereof, are preferred over the preproteins. The proteases may be further modified by the cells producing them after production of the polypeptide chain, for example by linkage of sugar molecules, formylation, amination, etc. Such modifications are post-translational modifications and may, but do not necessarily, exert an influence on the function of the protease.

The mature protease may furthermore also be truncated at its N-terminal and/or C-terminal end, such that a protease truncated relative to SEQ ID no. 1 or SEQ ID no. 2 or SEQ ID no. 3, i.e. a fragment, is present in the washing or cleaning agent according to the invention. All statements of identity relate in this case to that domain in which the respective fragment is assigned in a SEQ ID no. 1 alignment. The respective fragment does, however, in any event contain those positions which are assigned to positions 3, 4, 99 and/or 199 in an alignment with SEQ ID no. 1, and here comprises modifications corresponding to those provided according to the invention. In addition, such a fragment is proteolytically active. A fragment which is further preferred in this respect comprises an amino acid sequence which, over a length of at least 100 or at least 110, 120, 130, 140, 150, 160, 170, 180, 190, 200, 210, 220, 230, 240, 250, 260, 265 or 266 contiguous amino acid positions, matches SEQ ID no. 1 or SEQ ID no. 2 or SEQ ID no. 3, taking account of the above-stated amino acids for position 99 and furthermore for positions 3 and/or 4 and/or 199 and/or 211. The cleaning performance and/or storage stability of a liquid washing or cleaning agent according to the invention comprising such a fragment more preferably correspond(s) at least to that of a washing or cleaning agent which contains a protease which comprises an amino acid sequence which corresponds to the amino acid sequence stated in SEQ ID no. 2 or SEQ ID no. 3, in each case determined as stated above.

An agent according to the invention contains the protease increasingly preferably in a quantity of $1\times10^{-8}$-5 wt. %, of 0.0001-3 wt. %, of 0.0005-1 wt. %, of 0.001 to 0.75 wt. % and more preferably of 0.005 to 0.5 wt. %, relative to active protein. An agent according to the invention contains the amylase increasingly preferably in a quantity of $1\times10^{-8}$-5 wt. %, of 0.0001-3 wt. %, of 0.0005-1 wt. %, of 0.001 to 0.75 wt. % and more preferably of 0.005 to 0.5 wt. %, relative to active protein. Protein concentration may be determined with the assistance of known methods, for example the BCA method (bicinchoninic acid; 2,2'-biquinolyl-4,4'-dicarboxylic acid) or the biuret method (A. G. Gornau, C. S. Bardawill and M. M. David, J. Biol. Chem., 177 (1948), pp. 751-766). Active protein concentration proceeds in this respect via a titration of the active centers using a suitable irreversible inhibitor (for proteases for example phenylmethylsulfonyl fluoride (PMSF)) and determining residual activity (cf. M. Bender et al., J. Am. Chem. Soc. 88, 24 (1966), pp. 5890-5913).

The protease and/or amylase may furthermore be adsorbed onto carrier substances and/or be embedded in encapsulating substances in order to protect them from premature inactivation. In the washing liquor, i.e. under conditions of use, the enzyme is then liberated and can carry out its catalytic action.

In a further embodiment of the invention, the washing or cleaning agent is characterized in that it further comprises a component which is selected from
i. an anionic and/or polyanionic substance, and/or
ii. a cationic and/or polycationic substance, and/or
iii. a substance comprising hydroxyl and/or polyhydroxyl group(s).

It has been found that adding such substances further enhances the cleaning performance of washing and cleaning agents, in particular of liquid washing or cleaning agents which contain proteases and amylases, in particular those as described above, in particular at comparatively low temperatures, in particular between 10° C. and 50° C., between 10° C. and 40° C., between 10° C. and 30° C. and/or between 20° C. and 40° C. In particular in combination with a protease to be used according to the invention, a synergistic action occurs, above all with regard to the removal of at least one type of protease-sensitive soiling, in particular one as stated above.

The substances indicated above under i. are anionic or polyanionic substances, i.e. these substances bear at least one and preferably a number of negative charges. The substances are preferably a polymer with at least one negatively charged monomer, preferably with a plurality of negatively charged monomers. According to the invention this polymer is therefore preferably a negatively charged polymer. Preference is given, for example, to polymers of organic acids or the salts thereof, in particular polyacrylates and/or polysaccharide acids and/or polyacrylate copolymers and/or polysaccharide copolymers. In this respect, further preferred compounds are polyacrylic sulfonates or polycarboxylates and the salts thereof, copolymers or salts of the copolymers.

Examples of substances which are more preferably to be used are Acusol 587D (polyacrylic sulfonate; Rohm & Haas/Dow Chemical), Acusol 445N (polycarboxylate sodium salt; Rohm & Haas/Dow Chemical), Acusol 590 (polyacrylate copolymer; Rohm & Haas/Dow Chemical), Acusol 916N (polycarboxylate sodium salt; Rohm & Haas/Dow Chemical), Sokalan CP42 (modified polycarboxylate sodium salt; BASF), Sokalan PA 30CL (polycarboxylate sodium salt; BASF), Dequest P 9000 (polymaleic acid;

Thermphos), alginic acid, poly-2-acrylamido-2-methyl-1-propanesulfonic acid, poly-4-styrenesulfonic acid-co-maleic acid sodium salt, poly-acrylamido-co-acrylic acid sodium salt, polymethacrylic acid sodium salt, poly-methyl vinyl ether-alt-maleic acid or polyvinylsulfonic acid sodium salt.

The substances indicated above under ii. are cationic or polycationic substances, i.e. these substances bear at least one and preferably a plurality of positive charges. The substances are preferably a polymer with at least one positively charged monomer, preferably with a plurality of positively charged monomers. According to the invention this polymer is therefore preferably a positively charged polymer. Examples of compounds preferred in this respect are salts of polyamines, polyethyleneimines or the copolymers thereof, salts of polyallylamines, salts of polydiallyl dimethyl ammonium compounds or poly(acrylamide-co-diallyl dimethyl ammonium) compounds.

The substances indicated under iii. are substances which comprise at least one hydroxyl and/or polyhydroxyl group and preferably a plurality of hydroxyl and/or polyhydroxyl groups. In this respect, preference is given for example to polyvinyl alcohols, for example those available under the trade name Mowiol (Kremer Pigmente GmbH & Co. KG).

It is expressly pointed out at this point that a specific substance may belong to one or more of above-stated groups i. to iii. For example, it may be an anionic polymer, which comprises one or more hydroxyl and/or polyhydroxyl group(s). Such a substance then belongs to groups i. and iii. A cationic polymer which comprises one or more hydroxyl and/or polyhydroxyl group(s) likewise belongs to groups ii. and iii.

It is likewise possible for the purposes of the present invention to use derivatives of the substances stated above as belonging to i., ii. or iii. For the purposes of the present application a derivative is understood to be a substance which is chemically modified on the basis of one of the above-stated substances, for example by the conversion of a side chain or by covalent bonding of another compound to the substance. Such a compound may for example be low molecular weight compounds such as lipids or mono-, oligo- or polysaccharides or amines or amine compounds. The substance may furthermore be glycosylated, hydrolyzed, oxidized, N-methylated, N-formylated, N-acetylated or contain methyl, formyl, ethyl, acetyl, t-butyl, anisyl, benzyl, trifluoroacetyl, N-hydroxysuccinimide, t-butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, 2,2,5,7,8-pentamethylchromanyl-6-sulfonyl. A derivative is likewise understood to mean covalent or non-covalent bonding of the substance to a macromolecular carrier, or equally also non-covalent inclusion in suitable macromolecular cage structures. Coupling reactions with other macromolecular compounds, such as for instance polyethylene glycol, may also be undertaken. Further preferred chemical modifications are the modification of one or more of the chemical groups —COOH, —OH, =NH, —$NH_2$, —SH to —COOR, —OR, —NHR, —NR2, —NHR, —NR, —SR; wherein:

R is —CH=CH—R2, —C≡C—R2, —C(R2)=$CH_2$, —C(R2)=C(R3), —CH=NR2, —C(R2)=N—R3, a 4-7 C ring system with or without substitution, a 4-7 nitrogen heterocycle with or without substitution, or a $C_2$ to $C_8$ chain with 1 to 5 double or triple bonds with substitutions selected from R1, R2, or R3, wherein —R1 is H, —R, —$NO_2$, —CN, halide substituent, —$N_3$, —$C_{1-8}$ alkyl, —$(CH_2)_nCO_2R2$, —$C_{2-8}$-alkenyl-$CO_2R2$, —$O(CH_2)_nCO_2R2$, —C(O)NR2R3, —P(O)(OR2)$_2$, alkyl-substituted tetrazol-5-yl, —$(CH_2)_nO(CH_2)_n$-aryl, —NR2R3, —$(CH_2)_nOR2$, —$(CH_2)_nSR2$, —N(R2)C(O)R3, —S($O_2$)NR2R3, —N(R2)S($O_2$)R3, —$(CHR2)_nNR2R3$, —C(O)R3, $(CH_2)_nN(R3)C(O)R3$, —N(R2)CR2R3, substituted or unsubstituted $(CH_2)_n$-cycloalkyl, substituted or unsubstituted $(CH_2)$N-phenyl, or -cycle; wherein n is a number greater than 1;

—R2 is H, halide substituent, alkyl, haloalkyl, —$(CH_2)_n$-phenyl, —$(CH_2)_{1-3}$-biphenyl, —$(CH_2)$1-4-Ph-N($SO_2$—$C_{1-2}$-alkyl)$_2$, —CO(CHR1)$_n$—OR1, —(CHR1)$_n$-heterocycle, —(CHR1)$_n$—NH—CO—R1, —(CHR1)$_n$—NH—$SO_2R1$, —(CHR1)$_n$-Ph-N($SO_2$—$C_{1-2}$-alkyl)$_2$, —(CHR1)$_n$—C(O)(CHR1)-NHR1, —(CHR1)$_n$—C(S)(CHR1)-NHR1, —$(CH_2)_nO(CH_2)_nCH_3$, —$CF_3$, —$C_{2-5}$ acyl, —(CHR1)$_n$OH, —(CHR1)$_nCO_2R1$, —(CHR1)$_n$—O-alkyl, —(CHR1)$_n$—O—$(CH_2)_n$—O-alkyl, —(CHR1)$_n$—S-alkyl, —(CHR1)$_n$—S(O)-alkyl, —(CHR1)$_n$—S($O_2$)-alkyl, —(CHR1)$_n$—S($O_2$)—NHR3, —(CHR3)$_n$—$N_3$, —(CHR3)$_n$NHR4, a $C_2$ to $C_8$ chain alkene chain with 1 to 5 double bonds, a $C_2$ to $C_8$ chain alkyne chain with 1 to 5 triple bonds, substituted or unsubstituted —(CHR3)$_n$-heterocycle, substituted or unsubstituted saturated or unsaturated —(CHR3)$_n$-cycloalkyl; wherein n is a number greater than 1 and R1 and R3 may be identical or different;

—R3 is H, —OH, —CN, substituted alkyl, —$C_2$ to $C_8$ alkenyl, substituted or unsubstituted cycloalkyl, —N(R1)R2, saturated or unsaturated $C_5$ to $C_7$ heterocycle or heterobicycle of 4 to 7 C atoms, —NR1, —NR2, —NR1R2 consisting of a saturated or unsaturated heterocycle or a heterobicycle of 4 to 7 C atoms;

—R4 is H, —$(CH_2)_nOH$, —C(O)OR5, —C(O)SR5, —$(CH_2)_nC(O)NR6R7$, —O—C(O)—O—R6, an amino acid or a peptide; wherein n is a number between 0 and 4;

—R5 is H,

—R6 is —C(R7)-$(CH_2)_n$—O—C(O)—R8, —$(CH_2)_n$—C(R7)-O—C(O)R8, —$(CH_2)_n$—C(R7)-O—C(O)—O—R8, or —C(R7)-$(CH_2)_n$—O—C(O)—O—R8; wherein n is a number between 0 and 4; and —R7 and R8 are in each case H, alkyl, substituted alkyl, aryl, substituted aryl, alkenyl, substituted alkenyl, alkynyl, substituted alkynyl, heterocycle, substituted heterocycle, alkylaryl, substituted alkylaryl, cycloalkyl, substituted cycloalkyl, or $CH_2CO_2$ alkyl, wherein R7 and R8 may be identical or different.

According to the invention it is additionally possible to use all possible combinations of the substances stated above as belonging to i., ii. or iii. and/or the derivatives thereof.

A liquid washing or cleaning agent according to the invention may be used as such or after dilution with water for cleaning textiles and/or hard surfaces. Such a dilute solution may readily be produced by diluting a portion of the agent in a further quantity of water in specific ratios by weight of agent:water and optionally this dilution is shaken to ensure uniform distribution of the agent in the water. Possible weight or volume ratios of the dilutions are from 1:0 agent:water to 1:10,000 or 1:20,000 agent:water, preferably from 1:10 to 1:2000 agent:water.

All liquid or flowable presentations may here serve as liquid washing or cleaning agents. "Flowable" for the purposes of the present application means agents which can be poured and may exhibit viscosities of up to several tens of thousand mPa·s. Viscosity may be measured with conventional standard methods (for example Brookfield LVT-II viscosimeter at 20 rpm and 20° C., spindle 3) and is preferably in the range from 5 to 30,000 mPa·s. Preferred agents have viscosities of 10 to 15,000 mPa·s, wherein values of between 120 and 8000 mPa·s are more preferred. A liquid washing or cleaning agent for the purposes of the present invention may therefore also take the form of a gel or a paste, it may be present as a homogeneous solution or suspension, and for example be formulated as a sprayable or other conventional presentation. Washing agents include all conceivable types of washing agent, in particular washing agents for textiles, carpets or natural fibers. They may be provided for manual and/or also machine use. Washing agents further include washing auxiliaries, which may be added to the actual washing agent for manual or machine washing of textiles, to achieve a further effect. Cleaning agents include all agents, likewise occurring in all the stated presentations, for cleaning and/or disinfecting hard surfaces, manual and automatic dishwashing agents, carpet cleaners, scouring agents, glass cleaners, WC rimblocks, etc. Finally, textile pre- and post-treatment agents are on the one hand those agents with which an item of laundry is brought into contact before actual washing, for example to partially dissolve stubborn soiling, and on the other hand those which in a step downstream of the actual washing process impart to the washed item further desirable characteristics such as pleasant handle, absence of creases or low static charge. The latter agents include inter alia rinse conditioners. Disinfectants are for example hand disinfectants, surface disinfectants and instrument disinfectants, which may likewise occur in the stated presentations.

In a further preferred embodiment of the invention, the washing or cleaning agent is characterized in that it comprises at least one further ingredient, in particular an ingredient which is selected from the group consisting of phosphonate, surfactant, builder, nonaqueous solvent, acid, water-soluble salt, thickener and combinations hereof.

Phosphonates are salts and organic compounds, in particular esters, of phosphonic acid. Primary ($M'H_2PO_3$ or $HP(O)(OH)(OM')$) and secondary ($M'_2HPO_3$ or $HP(O)(OM')_2$) phosphonates exist as salts, wherein M' denotes a monovalent metal. These inorganic phosphonates are also known as primary or secondary phosphites. Inorganic phosphonates arise for example by reacting phosphonic acid $HP(O)(OH)_2$, in particular the stable tautomeric form of phosphorous acid, with one (primary) or two (secondary) equivalents of base, for example alkali metal hydroxide. For the purposes of the present invention organic P-substituted phosphonates which comprise a phosphorus-carbon bond are preferred (organophosphorus compounds). Their general structure is $R1P(O)(OR2)_2$, with R1 and/or R2=alkyl, aryl or H, wherein the alkyl or aryl residues comprise further substitutions or may bear further chemical groups. Organic P-substituted phosphonates arise for example as a result of the Michaelis-Arbusov reaction. Many of these phosphonates are soluble in water. Some industrially important phosphonates additionally bear amino group(s) of the type $NR—(CH_2)_x—PO(OH)_2$(R=alkyl, aryl or H). Some of these aminophosphonates have structural similarities with complexing agents such as EDTA, NTA or DTPA and have a similar function. More preferred phosphonates for the purposes of the present invention include in particular organophosphonates such as for example 1-hydroxyethane-1,1-diphosphonic acid (HEDP), aminotri(methylenephosphonic acid) (ATMP, also known as aminotris(methylenephosphonic acid) or nitrilotris(methylenephosphonic acid) (NTMP)), diethylenetriaminepenta(methylenephosphonic acid) (DTPMP or DETPMP or DTPNT), ethylenediaminetetra (methylenephosphonic acid) (EDTMP, also known as ethylenediaminetetra(methylenephosphonic acid)) and 2-phosphonobutane-1,2,4-tricarboxylic acid (PBS-AM, also known as 2-phosphonobutane-1,2,4-tricarboxylic acid or 3-carboxy-3-phosphonoadipic acid), which are usually used in the form of the ammonium or alkali metal salts thereof. Diethylenetriaminepenta(methylenephosphonic acid) sodium is more preferred. Such a phosphonate is obtainable for example under the trade name Dequest® 2066 (Thermphos).

The phosphonate is preferably present in the washing or cleaning agent in a quantity of 0.01 to 2.5 wt. % and increasingly preferably of 0.02 to 2 wt. %, of 0.03 to 1.5 wt. % and in particular of 0.05 to 1 wt. %.

Anionic, nonionic, zwitterionic and/or amphoteric surfactants may be used as surfactant(s). From an applicational standpoint mixtures of anionic and nonionic surfactants are preferred. The total surfactant content of the liquid washing or cleaning agent liquid is preferably below 60 wt. % and more preferably below 45 wt. %, relative to the total liquid washing or cleaning agent.

Suitable nonionic surfactants include alkoxylated fatty alcohols, alkoxylated fatty acid alkyl esters, fatty acid amides, alkoxylated fatty acid amides, polyhydroxy fatty acid amides, alkylphenol polyglycol ethers, amine oxides, alkyl polyglucosides and mixtures thereof.

Alkoxylated, advantageously ethoxylated, in particular primary alcohols with preferably 8 to 18 C atoms and on average 1 to 12 mol of ethylene oxide (EO) per mol of alcohol, in which the alcohol residue may be linear or preferably methyl-branched in position 2 or may contain linear and methyl-branched residues in the mixture, as they are usually present in oxo alcohol residues, are preferably used as nonionic surfactants. In particular, however, alcohol ethoxylates with linear residues prepared from alcohols of natural origin with 12 to 18 C atoms, for example from coconut, palm, tallow fat or oleyl alcohol, and on average 2 to 8 EO per mol of alcohol are preferred. Preferred ethoxylated alcohols include for example $C_{12-14}$ alcohols with 3 EO, 4 EO or 7 EO, $C_{9-11}$ alcohol with 7 EO, $C_{13-15}$ alcohols with 3 EO, 5 EO, 7 EO or 8 EO, $C_{12-18}$ alcohols with 3 EO, 5 EO or 7 EO and mixtures of these, such as mixtures of $C_{12-14}$ alcohol with 3 EO and $C_{12-18}$ alcohol with 7 EO. The stated degrees of ethoxylation are statistical averages which, for a specific product, may be an integer or a fractional number. Preferred alcohol ethoxylates have a narrow homologue distribution (narrow range ethoxylates, NRE). In addition to these nonionic surfactants, fatty alcohols with more than 12 EO may also be used. Examples of these are tallow fatty alcohol with 14 EO, 25 EO, 30 EO or 40 EO. Nonionic surfactants containing EO and PO groups together in one molecule may also be used according to the invention. Furthermore suitable are also a mixture of a (relatively highly) branched ethoxylated fatty alcohol and an unbranched ethoxylated fatty alcohol, such as for example a mixture of a $C_{16-18}$ fatty alcohol with 7 EO and 2-propylheptanol with 7 EO. More preferably, the washing, cleaning or post-treatment agent or washing auxiliary contains a $C_{12-18}$ fatty alcohol with 7 EO or a $C_{13-15}$ oxo alcohol with 7 EO as nonionic surfactant.

The content of nonionic surfactants in the washing or cleaning agent preferably amounts to 3 to 40 wt. %, preferably 5 to 30 wt. % and in particular 7 to 20 wt. %, in each case relative to the entire washing or cleaning agent.

In addition to the nonionic surfactants, the washing or cleaning agent may also contain anionic surfactants. Sulfonates, sulfates, soaps, alkyl phosphates, anionic silicone surfactants and mixtures thereof are preferably used as the anionic surfactant.

Surfactants of the sulfonate type which may here preferably be considered are $C_{9-13}$ alkyl benzene sulfonates, olefin sulfonates, i.e. mixtures of alkene and hydroxyalkane sulfonates and disulfonates, as are obtained, for example, from $C_{12-18}$ monoolefins with a terminal or internal double bond by sulfonation with gaseous sulfur trioxide and subsequent alkaline or acidic hydrolysis of the sulfonation products. $C_{12-18}$ alkane sulfonates and the esters of α-sulfofatty acids (ester sulfonates), for example the α-sulfonated methyl esters of hydrogenated coconut, palm kernel or tallow fatty acids, are also suitable.

Preferred alk(en)yl sulfates are the alkali metal and in particular sodium salts of sulfuric acid semi-esters of $C_{12}$-$C_{18}$ fatty alcohols for example prepared from coco fatty alcohol, tallow fatty alcohol, lauryl, myristyl, cetyl or stearyl alcohol or $C_{10}$-$C_{20}$ oxo alcohols and those semi-esters of secondary alcohols of these chain lengths. $C_{12}$-$C_{16}$ alkyl sulfates and $C_{12}$-$C_{15}$ alkyl sulfates and $C_{14}$-$C_{15}$ alkyl sulfates are preferred because of their washing characteristics. 2,3-Alkyl sulfates are also suitable anionic surfactants.

The sulfuric acid monoesters of straight-chain or branched $C_{7-21}$ alcohols ethoxylated with 1 to 6 mol of ethylene oxide are also suitable, such as 2-methyl-branched $C_{9-11}$ alcohols with on average 3.5 mol of ethylene oxide (EO) or $C_{12-18}$ fatty alcohols with 1 to 4 EO.

Soaps are also preferred anionic surfactants. Saturated and unsaturated fatty acid soaps are in particular suitable, such as the salts of lauric acid, myristic acid, palmitic acid, stearic acid, (hydrogenated) erucic acid and behenic acid and in particular soap mixtures derived from natural fatty acids, for example coconut, palm kernel, olive oil or tallow fatty acids.

The anionic surfactants including soaps may be present in the form of the sodium, potassium, magnesium or ammonium salts thereof. The anionic surfactants are preferably present in the form of the sodium salts thereof. Further preferred counterions for the anionic surfactants are also the protonated forms of choline, triethylamine or methylethylamine.

The anionic surfactant content of a washing or cleaning agent may amount to 1 to 40 wt. %, preferably 5 to 30 wt. % and particularly preferably 10 to 25 wt. %, in each case relative to the entire washing or cleaning agent.

Possible builders which may be contained in the washing or cleaning agent are in particular silicates, aluminum silicates (in particular zeolites), carbonates, salts of organic di- and polycarboxylic acids and mixtures of these substances.

Organic builders which may be present in the washing or cleaning agent are, for example, polycarboxylic acids, which are usable in the form of the sodium salts thereof, wherein polycarboxylic acids are taken to mean those carboxylic acids which bear more than one acid function. These are, for example, citric acid, adipic acid, succinic acid, glutaric acid, malic acid, tartaric acid, maleic acid, fumaric acid, saccharic acids, aminocarboxylic acids, nitrilotriacetic acid (NTA), methylglycinediacetic acid (MGDA) and the derivatives thereof and mixtures of these. Preferred salts are the salts of polycarboxylic acids such as citric acid, adipic acid, succinic acid, glutaric acid, tartaric acid, saccharic acids and mixtures of these.

Polymeric polycarboxylates are furthermore suitable as builders. These are for example the alkali metal salts of polyacrylic acid or of polymethacrylic acid, for example those with a relative molecular mass of 600 to 750,000 g/mol.

Suitable polymers are in particular polyacrylates which preferably have a molecular mass of 1,000 to 15,000 g/mol. Due to their superior solubility, the short-chain polyacrylates from this group may in turn be preferred, these having molar masses of 1000 to 10,000 g/mol, and more preferably of 1000 to 5000 g/mol.

Also suitable are copolymeric polycarboxylates, in particular those of acrylic acid with methacrylic acid and acrylic acid or methacrylic acid with maleic acid. In order to improve water solubility, the polymers may also contain allylsulfonic acids, such as allyloxybenzenesulfonic acid and methallylsulfonic acid, as a monomer.

Preferably, however, soluble builders, such as for example citric acid, or acrylic polymers with molar masses of 1000 to 5000 g/mol are preferably used in the liquid washing or cleaning agents.

The molar masses indicated for polymeric polycarboxylates comprise for the purposes of this document weight-average molar masses $M_w$ of the respective acid form, these having in principle been determined by means of gel permeation chromatography (GPC), wherein a UV detector was used. Measurement was here made relative to an external polyacrylic acid standard, which supplies realistic molecular weight values as a result of its structural relationship to the polymers under investigation. These values differ markedly from the molecular weight values in which polystyrenesulfonic acids are used as the standard. The molar masses measured relative to polystyrenesulfonic acids are generally markedly higher than the molar masses indicated in the present document.

Such organic builder substances may, if desired, be present in quantities of up to 40 wt. %, in particular of up to 25 wt. % and preferably of 1 wt. % to 8 wt. %. Quantities close to the stated upper limit are preferably used in pasty or liquid, in particular water-containing, agents.

The washing or cleaning agents according to the invention are liquid and preferably contain water as the main solvent. In addition, nonaqueous solvents may be added to the washing or cleaning agent. Suitable nonaqueous solvents include mono- or polyhydric alcohols, alkanolamines or glycol ethers, provided they are water-miscible in the stated concentration range. The solvents are preferably selected from ethanol, n-propanol, i-propanol, butanols, glycol, propanediol, butanediol, glycerol, diglycol, diethylene glycol propyl ether, diethylene glycol monobutyl ether, hexylene glycol, ethylene glycol methyl ether, ethylene glycol ethyl ether, ethylene glycol propyl ether, ethylene glycol n-butyl ether, diethylene glycol methyl ether, diethylene glycol ethyl ether, propylene glycol methyl ether, propylene glycol ethyl ether, propylene glycol propyl ether, dipropylene glycol monomethyl ether, dipropylene glycol monoethyl ether, diisopropylene glycol monomethyl ether, diisopropylene glycol monoethyl ether, methoxytriglycol, ethoxytriglycol, butoxytriglycol, 1-butoxyethoxy-2-propanol, 3-methyl-3-methoxybutanol, propylene glycol t-butyl ether, di-n-octyl ether and mixtures of these solvents. It is, however, preferred for the washing or cleaning agents to contain a polyol as nonaqueous solvent. The polyol may in particular comprise glycerol, 1,2-propanediol, 1,3-propanediol, ethylene glycol, diethylene glycol and/or dipropylene glycol. More preferably, the washing or cleaning agent contains a mixture of a polyol and a monohydric alcohol. Nonaqueous solvents may be used in the washing or cleaning agents in quantities of between 0.5 and 15 wt. %, but preferably of below 12 wt. %.

In order to establish a desired pH value which is not automatically obtained by mixing the remaining components, the agents may contain acids which are compatible with the system and are environmentally compatible, in particular citric acid, acetic acid, tartaric acid, malic acid, lactic acid, glycolic acid, succinic acid, glutaric acid and/or adipic acid, as well as mineral acids, in particular sulfuric acid, or bases, in particular ammonium or alkali metal hydroxides. Such pH regulators are present in the agents in quantities of preferably no more than 20 wt. %, in particular of 1.2 wt. % to 17 wt. %.

An agent according to the invention may furthermore contain one or more water-soluble salts, which serve for example to adjust viscosity. The salts may be inorganic and/or organic. Usable inorganic salts are here preferably selected from the group comprising colorless water-soluble halides, sulfates, sulfites, carbonates, hydrogencarbonates, nitrates, nitrites, phosphates and/or oxides of alkali metals, of alkaline earth metals, of aluminum and/or of transition metals; ammonium salts may furthermore be used. Halides and sulfates of alkali metals are more preferred; the inorganic salt is therefore preferably selected from the group comprising sodium chloride, potassium chloride, sodium sulfate, potassium sulfate and mixtures thereof. Examples of organic salts which may be used are colorless water-soluble alkali metal, alkaline earth metal, ammonium, aluminum and/or transition metal salts of carboxylic acids. The salts are preferably selected from the group comprising formate, acetate, propionate, citrate, malate, tartrate, succinate, malonate, oxalate, lactate and mixtures thereof.

For thickening purposes, an agent according to the invention may contain one or more thickeners. The thickener is preferably selected from the group comprising xanthan, guar, carrageenan, agar-agar, gellan, pectin, locust bean flour and mixtures thereof. These compounds are effective thickeners even in the presence of inorganic salts. In one more preferred embodiment, the washing or cleaning agent contains xanthan as thickener, since xanthan thickens effectively even in the presence of elevated salt concentrations and prevents macroscopic separation of the continuous phase. In addition, the thickener stabilizes the continuous, low-surfactant phase and prevents macroscopic phase separation.

As an alternative or in addition, (meth)acrylic acid (co) polymers may also be used as thickeners. Suitable acrylic and methacrylic (co)polymers include, for example, the high molecular weight homopolymers, crosslinked with a polyalkenyl polyether, in particular an allyl ether of sucrose, pentaerythritol or propylene, of acrylic acid (INCI name according to the "International Dictionary of Cosmetic Ingredients" of "The Cosmetic, Toiletry, and Fragrance Association (CTFA)": Carbomer), which are also known as carboxyvinyl polymers. Such polyacrylic acids are obtainable inter alia under the trade names Polygel® and Carbopol®. The following acrylic acid copolymers are furthermore suitable: (i) copolymers of two or more monomers from the group of acrylic acid, methacrylic acid and the simple esters thereof, preferably formed with $C_{1-4}$ alkanols (INCI Acrylates Copolymer) which are for example obtainable under the trade names Aculyn®, Acusol® or Tego® Polymer; (ii) crosslinked high molecular weight acrylic acid copolymers, including for instance the copolymers of $C_{10-30}$ alkyl acrylates crosslinked with an allyl ether of sucrose or of pentaerythritol with one or more monomers from the group of acrylic acid, methacrylic acid and the simple esters thereof, preferably formed with $C_{1-4}$ alkanols (INCI Acrylates/C10-30 Alkyl Acrylate Crosspolymer) and are for example obtainable under the trade name Carbopol®. Further suitable polymers are (meth)acrylic acid (co)polymers of the Sokalan® type.

It may be preferable for the washing or cleaning agent according to the invention to contain a (meth)acrylic acid (co)polymer in combination with a further thickener, preferably xanthan. The washing or cleaning agent may contain 0.05 to 1.5 wt. % and preferably 0.1 to 1 wt. %, in each case relative to the entire washing or cleaning agent, of thickener. The quantity of thickener used is here dependent on the type of thickener and the desired degree of thickening.

Liquid or pasty products according to the invention in the form of solutions containing conventional solvents are generally produced by simply mixing the constituents, which may be introduced into an automatic mixer as an undissolved material or as a solution.

Washing or cleaning agents according to the invention may contain solely a protease and an amylase as described. Alternatively, they may also contain further hydrolytic enzymes or other enzymes in a concentration convenient for the efficacy of the agent. The invention thus further provides agents which additionally comprise one or more further enzymes, wherein in principle all enzymes established for this purpose in the prior art may be used. Further preferably usable enzymes are any enzymes which can carry out a catalytic activity in the agent according to the invention, in particular a protease, amylase, cellulase, hemicellulase, mannanase, tannase, xylanase, xanthanase, xyloglucanase, β-glucosidase, pectinase, carrageenase, perhydrolase, oxidase, oxidoreductase or a lipase, and the mixtures thereof. Further enzymes are advantageously present in the agent in each case in a quantity of $1\times10^{-8}$ to 5 weight percent relative to active protein. Each further enzyme is increasingly preferably present agents according to the invention in a quantity of $1\times10^{-7}$-3 wt. %, of 0.00001-1.5 wt. %, of 0.00005-1 wt. %, of 0.0001 to 0.75 wt. % and more preferably of 0.0005 to 0.5 wt. %, relative to active protein. More preferably, the enzymes exhibit synergistic cleaning performance with regard to their action relative to specific soiling or stains, i.e. the enzymes contained in the agent composition assist one another's cleaning performance. Particularly preferably, such a synergistic action is present between the protease according to the invention and a further enzyme of an agent according to the invention, including in particular between the stated protease and the amylase and/or a lipase and/or a mannanase and/or a cellulase and/or a pectinase. Synergistic effects may occur not only between different enzymes, but also between one or more enzymes and further ingredients of the agent according to the invention.

In a further embodiment of the invention, the washing or cleaning agent is characterized in that it is an automatic dishwashing agent. As defined in the present application, automatic dishwashing agents are compositions which may be used for cleaning soiled dishes in an automatic dishwashing method. The automatic dishwashing agents according to the invention thus differ, for example, from automatic rinse aids, which are always used in combination with automatic dishwashing agents and do not themselves carry out any cleaning action. More stringent requirements are often applied to machine washed dishes than are applied to hand washed dishes. For instance, after machine cleaning, dishes should not only be completely free of food residues but should for example also not exhibit any whitish blemishes based on water hardness or other mineral salts which originate from dried water drops due to a lack of wetting agents. Modern automatic dishwashing agents satisfy these requirements by incorporating cleaning and/or conditioning and/or water softening and/or rinsing active substances and are for example known to the consumer as "2-in-1" or "3-in-1" dishwashing agents. Automatic dishwashing agents contain builders as an essential component for successful cleaning and rinsing. On the one hand, these builders increase the alkalinity of the washing liquor, wherein fats and oils are emulsified and saponified as alkalinity rises, and, on the other hand, reduce the water hardness of the washing liquor by complexing the calcium ions present in the aqueous liquor. In one further preferred development, the automatic dishwashing agent is enclosed in a water-soluble film. The film preferably comprises a polyvinyl alcohol (PVA) or consists of polyvinyl alcohol (PVA).

The invention further provides the use of a washing or cleaning agent according to the invention for removing soiling, in particular protease- and/or amylase-sensitive soiling, from textiles or hard surfaces, i.e. for cleaning textiles or hard surfaces. This is because agents according to the invention may, in particular due to the combination of protease and amylase contained therein, advantageously be used to remove corresponding soil from textiles or from hard surfaces. Embodiments of this aspect of the invention include for example hand laundering, manual removal of stains from textiles or hard surfaces or use in connection with a machine method. All factors, aspects and embodiments which have been described for washing or cleaning agents according to the invention are also applicable to this aspect of the invention. Express reference is therefore made at this point to the disclosure at corresponding points, it being pointed out that this disclosure also applies to the above use according to the invention.

The invention further provides a method for cleaning textiles or hard surfaces, wherein a washing or cleaning agent according to the invention is used in at least one of the method steps.

These include both manual and machine methods, wherein machine methods are preferred, due to their being more precisely controllable, for example in terms of the quantities used and periods of exposure. Methods for cleaning textiles are in general distinguished in that in two or more method steps various substances with a cleaning action are applied onto the material to be cleaned and, after the period of exposure, are washed off, or that the material to be cleaned is treated in some other manner with a washing agent or a solution or dilution of this agent. The same applies to methods for cleaning all materials other than textiles, in particular hard surfaces. Any conceivable washing or cleaning methods may be enhanced in at least one of the method steps by application of a washing or cleaning agent according to the invention and then constitute embodiments of the present invention. All factors, aspects and embodiments which have been described for washing or cleaning agents according to the invention are also applicable to this aspect of the invention. Express reference is therefore made at this point to the disclosure at corresponding points, it being pointed out that this disclosure also applies to the above methods according to the invention.

In a preferred embodiment, the method is characterized in that the amylase is present in the washing liquor in a concentration of $1\times10^{-10}$-0.2 wt. %, of 0.000001-0.12 wt. %, of 0.000005-0.04 wt. %, of 0.00001 to 0.03 wt. % and more preferably of 0.00005 to 0.02 wt. %, and/or in that the protease is present in the washing liquor in a concentration of $1\times10^{-10}$-0.2 wt. %, of 0.000001-0.12 wt. %, of 0.000005-0.04 wt. %, of 0.00001 to 0.03 wt. % and more preferably of 0.00005 to 0.02 wt. %, wherein the stated values relate to active protein in the washing liquor. In a further preferred embodiment, the method is characterized in that it is carried out at a temperature of between 10° C. and 60° C., preferably between 20° C. and 50° C. and more preferably of between 30° C. and 50° C.

Proteases used in agents according to the invention may advantageously be used, in accordance with the above explanations, in washing and cleaning agents according to the invention as well as in methods, in particular washing and cleaning methods. They may thus advantageously be used to provide proteolytic activity in corresponding agents.

The present invention further provides the use of a protease which comprises an amino acid sequence which, over the entire length thereof, is at least 70% identical to the amino acid sequence stated in SEQ no. 1 and, in the numbering according to SEQ ID no. 1, has the amino acid substitution R99E or R99D in combination with at least two further amino acid substitutions which are selected from the group consisting of S3T, V4I and V199I, in order to provide a proteolytic activity in a liquid washing or cleaning agent which further comprises an amylase.

All factors, aspects and embodiments which have been described for washing or cleaning agents according to the invention are also applicable to the stated uses. Express reference is therefore made at this point to the disclosure at corresponding points, it being pointed out that this disclosure also applies to the above uses according to the invention.

Example: Determination of the Storage Stability of a Liquid Automatic Dishwashing Agent According to the Invention The base formulation was an amylase-containing biphasic liquid automatic dishwashing agent which was of the following composition (all values stated in weight percent):
(a) Enzyme Phase:

| Builder | 18.0 |
|---|---|
| Sugar alcohol | 12.0 |
| Nonionic surfactant ($C_8$-$C_{10}$ fatty alcohol ethoxylate with 22 EO) | 5.0 |
| Alkali compound (base) | 3.5 |
| Boric acid | 3.0 |
| Phosphonate (HEDP) | 1.5 |
| Amylase | 1.2 |
| Ca salt | 1.2 |
| Zn salt | 0.2 |
| Thickener | 1.0 |
| Dye, perfume, preservative | 0.3 |
| Water | ad 97 |

The amylase present was an α-amylase variant which, relative to the α-amylase AA560 according to SEQ ID no. 4, has the following sequence modifications in the numbering of α-amylase AA560: R118K, D183* (deletion), G184* (deletion), N195F, R320K, R458K (Novozymes).
(b) Alkaline Phase:

| Builder | 12.0 |
|---|---|
| Sodium carbonate | 10.0 |
| Sulfopolymer | 7.0 |
| Alkali compound (base) | 4.0 |
| Monoethanolamine | 3.5 |
| Phosphonate (HEDP) | 4.0 |
| Thickener | 1.0 |
| Dye, perfume, preservative | 0.3 |
| Water | ad 100 |

The enzyme phase of the base formulation was combined for the various test batches with in each case 3 wt. % of preparations of the following proteases (resulting in each case in 0.5 wt. % active protein):

Batch 1: enhanced performance variant of the protease from *Bacillus lentus* according to SEQ ID no. 2 of WO2011/032988 (reference);

Batch 2: protease according to SEQ ID no. 2 (SEQ ID no. 1+S3T+V4I+R99E+V199I).

Cleaning performance was determined by apportioning the two phases in identical proportions (in each case 20 g per phase). Washing was performed in a pH value range between pH 9 and pH 10 in a G698SC dishwashing machine from Miele in a volume of 4 liters for a period of 60 minutes at a temperature of 50° C.

Dishes with the following soiling were used: milk (A), minced meat (B), egg yolk (C), porridge oats (D) and starch (E).

Cleaning performance is evaluated visually using the standard IKW method on a scale from 1 to 10, wherein a value of 10 is the best rating (no discernible residue).

The washing agents of batches 1 and 2 were tested with regard to their cleaning performance before and after storage for four weeks at 40° C. The results are shown in Table 1 below:

TABLE 1

| Soiling | A | B | C | D | E |
|---|---|---|---|---|---|
| Batch 1 before storage | 5.6 | 10.0 | 5.2 | 7.7 | 9.6 |
| Batch 2 before storage | 5.2 | 10.0 | 5.7 | 7.8 | 9.8 |
| Batch 1 after storage | 5.1 | 2.8 | 1.7 | 2.0 | 3.4 |
| Batch 2 after storage | 5.2 | 7.7 | 3.0 | 5.1 | 4.0 |

After four weeks' storage at 40° C., it is clear that the composition according to the invention, thanks to the protease contained therein, exhibits distinctly improved cleaning performance, in particular on protease-sensitive types of soiling B and C (proteolytic cleaning performance). In particular, cleaning performance on amylase-sensitive types of soiling D and E is also improved (amylolytic cleaning performance). In certain embodiments, the protease of Batch 2 having an amino acid sequence which, over the entire length thereof, is at least 95% identical to the amino acid sequence stated in SEQ ID no. 1 and, in the numbering according to SEQ ID no. 1, has the amino acid substitution R99E, in combination with the amino acid substitutions S3T, V4I and V199I. The protease of Batch 2 having the amino acid substitutions exhibits improved cleaning performance after storage as compared to a protease according to SEQ ID no. 1 free of the amino acid substitutions S3T, V4I and V199I after storage. In certain embodiments, the amylase which is an α-amylase variant of the α-amylase AA560 having an amino acid sequence which, over the entire length thereof, is at least 95% identical to the amino acid sequence stated in SEQ ID no. 4, and in the numbering according to SEQ ID no. 4, has the sequence modifications R118K, D183* (deletion), G184* (deletion), N195F, R320K, and R458K. The amylase exhibits improved cleaning performance after storage with the protease of Batch 2 as compared to after storage with a protease according to SEQ ID no. 1 free of the amino acid substitutions S3T, V4I and V199I.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A liquid washing or cleaning agent comprising:
   (a) a protein comprising a protease having an amino acid sequence which, over the entire length thereof, is at least 95% identical to the amino acid sequence stated in SEQ ID no. 1 and, in the numbering according to SEQ ID no. 1, has the amino acid substitution R99E or R99D, in combination with the amino acid substitutions S3T, V4I and V199I; and
   (b) a protein comprising an amylase which is an α-amylase variant of the α-amylase AA560 having an amino acid sequence which, over the entire length thereof, is at least 95% identical to the amino acid sequence stated in SEQ ID no. 4, and in the numbering according to SEQ ID no. 4, has the sequence modifications R118K, D183* (deletion), G184* (deletion), N195F, R320K, and R458K;
   wherein the protease having the amino acid substitutions exhibits improved cleaning performance after storage as compared to a protease according to SEQ ID no. 1 free of the amino acid substitutions S3T, V4I and V199I after storage, and
   wherein the amylase having the amino acid substitutions exhibits improved cleaning performance after storage with the protease having the amino acid substitutions as compared to after storage with a protease according to SEQ ID no. 1 free of the amino acid substitutions S3T, V4I and V199I.

2. The washing or cleaning agent according to claim 1, wherein the protease comprises an amino acid sequence which, over the entire length thereof, is at least 95% identical to the amino acid sequence stated in SEQ ID no. 1 and, in the numbering according to SEQ ID no. 1, has the amino acid substitution R99D in combination with the amino acid substitutions S3T, V4I and V199I.

3. The washing or cleaning agent according to claim 1, further comprising a component selected from the group consisting of:
   i. an anionic and/or polyanionic substance;
   ii. a cationic and/or polycationic substance; and
   iii. a substance comprising hydroxyl and/or polyhydroxyl group(s).

4. The washing or cleaning agent according claim 1, comprising at least one further ingredient selected from the group consisting of phosphonate, surfactant, builder, non-aqueous solvent, acid, water-soluble salt, thickener and combinations hereof.

5. The washing or cleaning agent according to claim 1, comprising at least one further enzyme selected from the group consisting of: protease, amylase, cellulase, hemicellulase, mannanase, tannase, xylanase, xanthanase, xyloglucanase, β-glucosidase, pectinase, carrageenase, perhydrolase, oxidase, oxidoreductase or a lipase, and mixtures thereof.

6. A method for cleaning textiles or hard surfaces, wherein a washing liquor containing the washing or cleaning agent according to claim 1 contacts the textile or hard surface in at least one method step.

7. The method according to claim 6, wherein the amylase is present in the washing liquor in a concentration of $1 \times 10^{-10}$ to 0.2 wt. %, and in that the protease is present in the washing liquor in a concentration of $1 \times 10^{10}$ to 0.2 wt %.

8. The method according to claim 7, wherein it is carried out at a temperature of between 10° C. and 60° C.

9. A liquid washing or cleaning agent comprising:
   (a) a protein comprising a protease having an amino acid sequence which, over the entire length thereof, is at least 95% identical to the amino acid sequence stated in SEQ ID no. 1 and, in the numbering according to SEQ ID no. 1, has the amino acid substitution R99E or R99D, in combination with the amino acid substitutions S3T, V4I and V199I; and
   (b) a protein comprising an amylase which is an α-amylase variant of the α-amylase AA560 having an amino acid sequence which, over the entire length thereof, consists of, in the numbering according to SEQ ID no. 4, the sequence modifications R118K, D183* (deletion), G184* (deletion), N195F, R320K, and R458K;
   wherein the protease having the amino acid substitutions exhibits improved cleaning performance after storage as compared to a protease according to SEQ ID no. 1 free of the amino acid substitutions S3T, V4I and V199I after storage, and
   wherein the variant amylase having the amino acid substitutions exhibits improved cleaning performance after storage with the protease having the amino acid substitutions as compared to after storage with a protease according to SEQ ID no. 1 free of the amino acid substitutions S3T, V4I and V199I.

* * * * *

SEQUENCE LISTING

```
<160> NUMBER OF SEQ ID NOS: 4

<210> SEQ ID NO 1
<211> LENGTH: 269
<212> TYPE: PRT
<213> ORGANISM: Bacillus lentus

<400> SEQUENCE: 1

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110
```

-continued

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 2
<211> LENGTH: 269
<212> TYPE: PRT
<213> ORGANISM: Bacillus lentus

<400> SEQUENCE: 2

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala

```
            210                 215                 220
Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

<210> SEQ ID NO 3
<211> LENGTH: 269
<212> TYPE: PRT
<213> ORGANISM: Bacillus lentus

<400> SEQUENCE: 3

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Asp Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
    115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
    195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

<210> SEQ ID NO 4
<211> LENGTH: 485
<212> TYPE: PRT
<213> ORGANISM: Bacillus sp.

<400> SEQUENCE: 4

His His Asn Gly Thr Asn Gly Thr Met Met Gln Tyr Phe Glu Trp Tyr
```

```
1               5                    10                   15

Leu Pro Asn Asp Gly Asn His Trp Asn Arg Leu Arg Ser Asp Ala Ser
                20                  25                  30

Asn Leu Lys Asp Lys Gly Ile Ser Ala Val Trp Ile Pro Pro Ala Trp
                35                  40                  45

Lys Gly Ala Ser Gln Asn Asp Val Gly Tyr Gly Ala Tyr Asp Leu Tyr
 50                  55                  60

Asp Leu Gly Glu Phe Asn Gln Lys Gly Thr Ile Arg Thr Lys Tyr Gly
 65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
                115                 120                 125

Gln Glu Val Ser Gly Glu Tyr Thr Ile Glu Ala Trp Thr Lys Phe Asp
                130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
                180                 185                 190

Thr Glu Asn Gly Asn Tyr Asp Tyr Leu Met Tyr Ala Asp Ile Asp Met
                195                 200                 205

Asp His Pro Glu Val Val Asn Glu Leu Arg Asn Trp Gly Val Trp Tyr
                210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
                260                 265                 270

Gly Ala Ile Glu Asn Tyr Leu Asn Lys Thr Asn Trp Asn His Ser Val
                275                 280                 285

Phe Asp Val Pro Leu His Tyr Asn Leu Tyr Asn Ala Ser Lys Ser Gly
                290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Trp Phe Lys Pro Leu Ala
                340                 345                 350

Tyr Ala Leu Thr Leu Thr Arg Glu Gln Gly Tyr Pro Ser Val Phe Tyr
                355                 360                 365

Gly Asp Tyr Tyr Gly Ile Pro Thr His Gly Val Pro Ala Met Lys Ser
                370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430
```

```
Gly Ala Gly Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485
```